(12) United States Patent
Hur et al.

(10) Patent No.: US 10,935,472 B2
(45) Date of Patent: Mar. 2, 2021

(54) PUMPED COOLING SYSTEM IN GAS DETECTOR

(71) Applicant: Honeywell International Inc., Morris Plains, NJ (US)

(72) Inventors: SangHoon Hur, Seoul (KR); Changyoung Jung, Seoul (KR); Hyungwoo Baek, Seoul (KR); Jeffrey Lee, Seoul (KR)

(73) Assignee: Honeywell International Inc., Morris Plains, NJ (US)

( * ) Notice: Subject to any disclaimer, the term of this patent is extended or adjusted under 35 U.S.C. 154(b) by 258 days.

(21) Appl. No.: 15/914,889

(22) Filed: Mar. 7, 2018

(65) Prior Publication Data

US 2019/0277731 A1   Sep. 12, 2019

(51) Int. Cl.
   *G01N 1/22*   (2006.01)
(52) U.S. Cl.
   CPC ... *G01N 1/2273* (2013.01); *G01N 2001/2276* (2013.01); *G01N 2001/2282* (2013.01)
(58) Field of Classification Search
   CPC .................................................. G01N 1/2273
   USPC ......................................................... 73/31.02
   See application file for complete search history.

(56) References Cited

U.S. PATENT DOCUMENTS 6,456,095 B1   9/2002  Sorita et al.
2009/0185190 A1*  7/2009  Weinberger ............ G01N 21/45
            356/450
2012/0287418 A1* 11/2012  Scherer ............... G01N 21/3504
            356/51
2016/0178587 A1   6/2016  Basham

FOREIGN PATENT DOCUMENTS

CN          104442912 A    3/2015
WO       WO2015036725 A1   3/2015

OTHER PUBLICATIONS

English Translation of KR Office Action dated Aug. 18, 2020 for KR Application No. 10-2019-0020792.
KR Office Action dated Aug. 18, 2020 for KR Application No. 10-2019-0020792.

* cited by examiner

*Primary Examiner* — Walter L Lindsay, Jr.
*Assistant Examiner* — Philipmarcus T Fadul
(74) *Attorney, Agent, or Firm* — Alston & Bird LLP

(57) ABSTRACT

Embodiments relate to systems and methods for dissipating heat within a gas detector. A gas detector may comprise an airflow generator configured to generate a sample gas flow through the gas detector; a sample gas flow line configured to direct the sample gas flow within a housing of the gas detector from an inlet of the gas detector toward an outlet of the gas detector; a sensor, in fluid communication with the airflow generator via the sample gas flow line, configured to detect one or more potentially hazardous gases within the sample gas flow; and a heat sink, in fluid communication with the airflow generator and positioned after the sensor along the sample gas flow line, configured to transfer heat from an interior of the housing to the sample gas flow, wherein the sample gas flow is directed out of the housing via the outlet of the gas detector.

20 Claims, 3 Drawing Sheets

PUMPED COOLING SYSTEM IN GAS DETECTOR

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND

In hazardous work environments, workers may carry gas detectors with them as they work, to allow for detection of gas exposure. The gas detector may alert the user if exposure limits are reached while the user is wearing the gas detector. Gas detectors may comprise interfaces for communicating with the user, such as displays, lights, buzzers, and input buttons. Gas detectors may be configured with settings for alarms, exposure limits, display settings, light and buzzer settings, etc. Additionally, gas detectors may be in fixed locations and/or may be configured to test a sample gas remotely from the location where exposure is possible.

SUMMARY

In an embodiment, a gas detector may comprise a housing configured to contain the elements of the gas detector; an airflow generator located within the housing and configured to generate a sample gas flow through the gas detector; a sample gas flow line configured to direct the sample gas flow within the housing of the gas detector from an inlet of the gas detector toward an outlet of the gas detector; a sensor, located within the housing and in fluid communication with the airflow generator via the sample gas flow line, configured to detect one or more potentially hazardous gases within the sample gas flow; and a heat sink, located within the housing in fluid communication with the airflow generator and positioned after the sensor along the sample gas flow line, configured to transfer heat from an interior of the housing to the sample gas flow, wherein the sample gas flow is directed out of the housing via the outlet of the gas detector.

In an embodiment, a method for dissipating heat from the interior of a gas detector may comprise generating a sample gas flow through the gas detector via an airflow generator from an inlet of the gas detector toward an outlet of the gas detector; testing, by a sensor within the gas detector, the sample gas flow for one or more potentially hazardous gases; after testing the sample gas flow by the sensor, directing the sample gas flow toward an inlet of a heat sink located within a housing of the gas detector; transferring heat from the interior of the housing to the sample gas flow via the heat sink; and directing the sample gas flow out of the gas detector via an outlet of the gas detector.

In an embodiment, a gas detector may comprise an inlet configured to receive a sample gas flow; an outlet configured to exhaust the sample gas flow from the gas detector; an airflow generator configured to generate the sample gas flow through the gas detector from the inlet toward the outlet; a sensor in fluid communication with the airflow generator, configured to detect one or more potentially hazardous gases within the sample gas flow; and a heat sink in fluid communication with the airflow generator, positioned between the sensor and the outlet in the direction of the sample gas flow, and configured to transfer heat from an interior of the gas detector to the sample gas flow.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
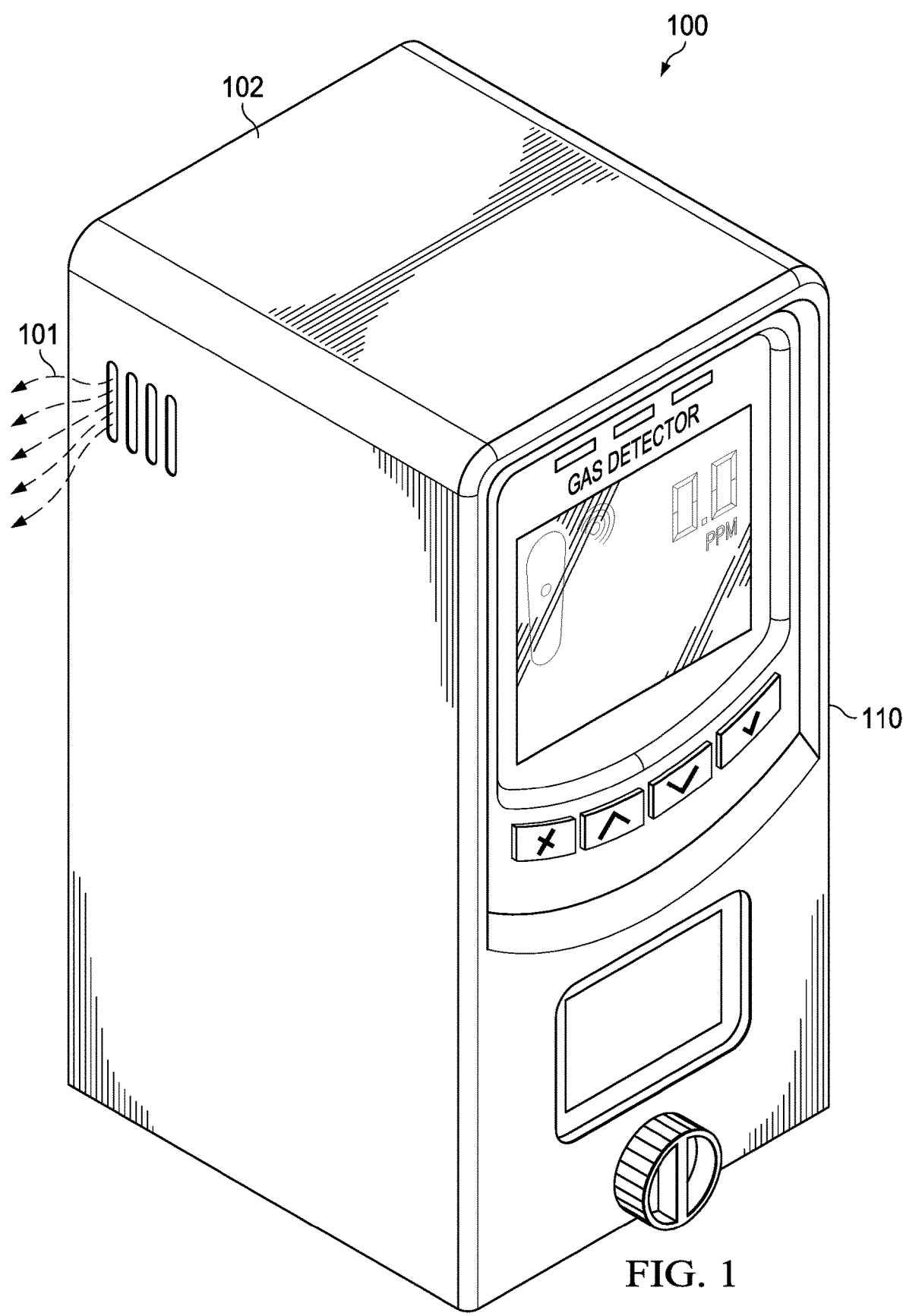
FIG. 1 illustrates a perspective view of a gas detector according to an embodiment of the disclosure.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Gas detectors typically comprise electronic elements (or components) and at least one airflow generator. In some embodiments, the airflow generator may be a pump. In operation, the electronic elements and the airflow generator (e.g. pump) may generate heat, causing the internal temperature of the gas detector to rise. Typical gas detectors may be cooled via convective cooling from the ambient air surrounding the gas detector. However, this type of cooling may not always be sufficient to dissipate the heat generated by the electronic elements and other components of the gas detector. If the internal temperature of the gas detector is not adequately controlled, the elevated temperature could cause damage to the electronic elements and other components of the gas detector. Additionally, as the capabilities of the gas detector are improved and increased and more processes are completed by the gas detector, the heat generated by the internal components may also increase.

The primary function of the gas detector may be to pull a sample gas flow to a sensor within the gas detector, and to determine when/if potentially hazardous gases are present within the sample gas flow. The sensed information may also be communicated to a user. Before the sample gas flow is tested by the sensor, it may be important to maintain the integrity of the sample gas flow. However, after the sample gas flow has been tested, the exhaust or outlet of the sample gas flow may be directed out of the gas detector, and may be discarded as waste. Therefore, any manipulation of the sample gas flow after it has passed through the sensor of the gas detector may not affect the accuracy of the sensor.

Embodiments of the disclosure include systems and methods for cooling the internal elements of a gas detector using the sample gas that is tested by the gas detector, after the sample gas has passed through the sensor of the gas detector. A heat sink may be incorporated into the housing of the gas detector, where the sample gas flow may be passed through the heat sink, and may absorb heat from the interior of the gas detector, and then may be directed out of the gas detector and discarded as waste. The heat sink may be positioned within the housing of the gas detector to effectively transfer heat from the electronic elements within the gas detector to the sample gas flow passing through the gas detector.

Referring now to FIG. 1, an exemplary gas detector 100 is shown where the gas detector 100 may comprise a housing 102, and optionally a front panel 110. The front panel 110 may comprise a user interface, such as a screen, buttons, lights, or other user interface elements. As described above, the gas detector 100 may generate heat 101 due to the operation of the electronic elements within the gas detector 100. As the capabilities of and processes completed by the gas detector 100 increase, the operation of the electronic elements may cause an increase in the generated heat within the housing 102.

Figure 2:
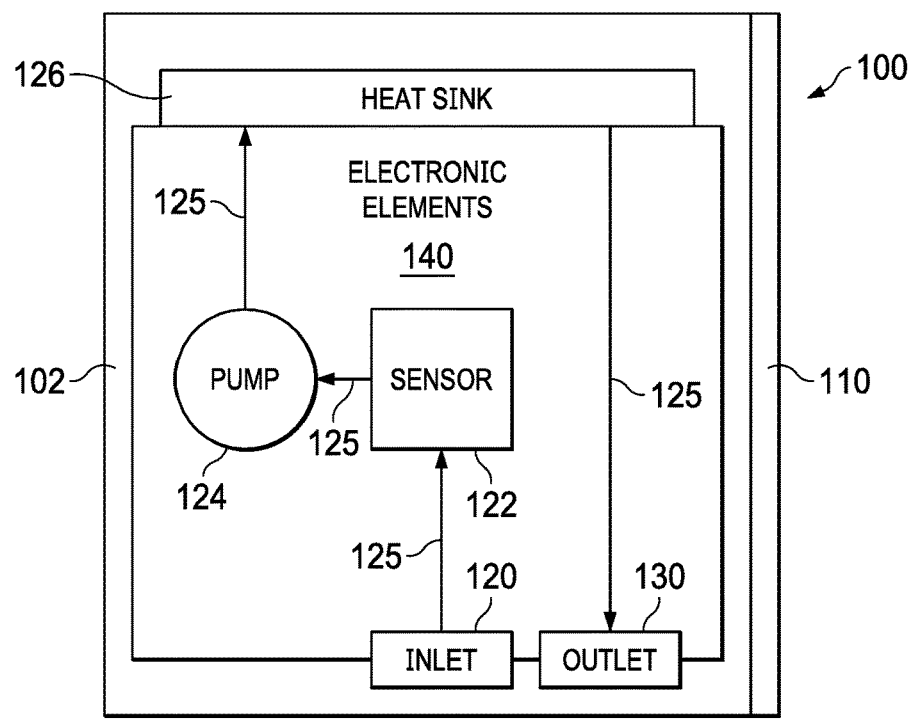
FIG. 2 illustrates a block diagram view of a gas detector according to an embodiment of the disclosure.

Referring to FIG. 2, a block diagram of an exemplary gas detector 100 is shown. As described in FIG. 1, the gas detector 100 may comprise a housing 102 and front panel 110. The gas detector 100 may comprise a plurality of electronic elements 140 located within the housing 102. These electronic elements 140 may comprise circuits, one or more power source, or other electronic elements 140 that may generate heat when in use.

Additionally, the gas detector may comprise a sensor 122 in fluid communication with an airflow generator, e.g., a pump 124, configured to draw sample gas to the sensor 122 from an inlet 120 of the gas detector 100. The inlet 120 may comprise a connector configured to attach to a sample gas feed (which may be tubing from an area potentially containing one or more hazardous gases). In the embodiment shown in FIG. 2, the pump 124 may be positioned after the sensor 122, along a sample gas flow line 125, but in other embodiments, the positions and/or orientations of the sensor 122 and pump 124 may be different.

In a typical gas detector, the sample gas would be sent to an outlet 130 after passing through the sensor 122 and pump 124. However, in the embodiment shown in FIG. 2, the sample gas (e.g., within the sample gas flow line 125) may be fed to a heat sink 126 located within the housing 102 of the gas detector 100 before being sent to the outlet 130 of the gas detector 100, where the heat sink 126 may be in fluid communication with the pump 124 and/or sensor 122. The heat sink 126 may be configured to transfer heat from the electronic elements 140 within the housing 102 to the sample gas as it flows through the heat sink 126. Then, the sample gas may be directed toward the outlet 130, via the sample gas flow line 125, and out of the housing 102 via the outlet 130. In some embodiments, the sample gas may be safely exhausted from the outlet 130.

In some embodiments, the heat sink 126 may be located within a top portion of the housing 102. In some embodiments, the heat sink 126 may be located adjacent to one or more electronic elements 140 that may generate heat when in operation. In some embodiments, the heat sink 126 may be located anywhere within the housing 102 of the gas detector 100.

In use, the heat sink 126 may allow heat to be absorbed by the sample gas flowing through the heat sink 126, thereby removing heat from the interior of the housing 102 of the gas detector 100. In some embodiments, the use of a heat sink 126 may prevent elevated temperatures within the gas detector 100 from interfering with the function of the sensor 122. Rather than using the surrounding ambient air to provide cooling to the gas detector 100 (which may not provide sufficient heat transfer/cooling), the sample gas flow that is already passing through the gas detector 100 may be used as the fluid medium in the heat sink 126.

In some embodiments, the heat sink 126 may be insulated and/or air tight, to prevent escape of the sample gas from the heat sink 126. In some embodiments, the sample gas may contain one or more toxic or potentially hazardous gases (that may be detected by the sensor 122). The potentially hazardous gases may comprise one or more of the following: hydrogen sulfide, ammonia, carbon monoxide, natural gas, phosgene, and/or organic compounds (e.g., volatile organic compounds, etc.).

As an example, using known heat transfer equations (e.g., Newton's law of cooling, Gnielinski correlation, thermal resistance, and/or other thermal characteristics), the heat transfer capabilities of the heat sink 126 may be determined based on the flow rate of the sample gas, the size of the heat sink 126, and other characteristics of the heat sink 126 and sample gas. In an example, when the sample gas flow is approximately 500 cubic centimeters per minute (cc/min) and the convection area of the heat sink 126 is approximately 0.01 square meters ($m^2$), the estimated convection (from the interior of the housing 102 of the gas detector 100 to the sample gas flow) would be up to approximately 25.7° C. In some embodiments, the gases that make up the sample gas flow may affect the heat transfer characteristics of the sample gas.

Figure 3:
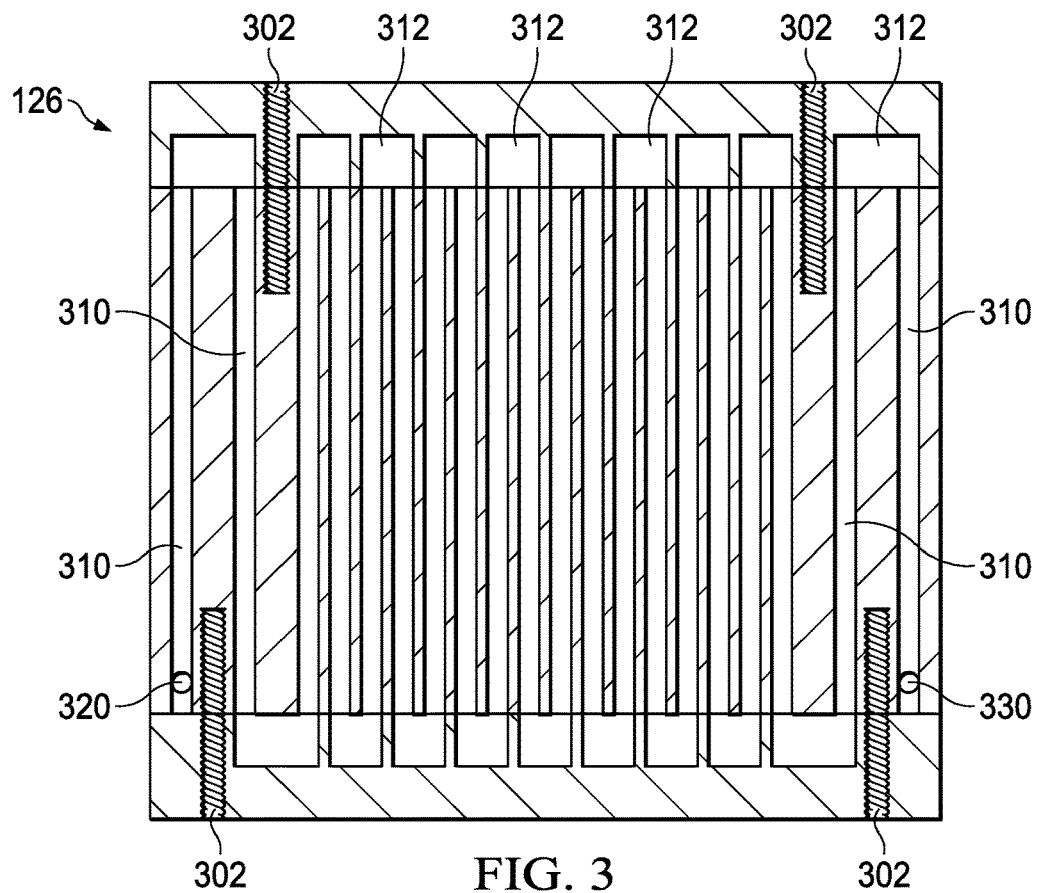
FIG. 3 illustrates a cross-sectional view of a heat sink according to an embodiment of the disclosure.
Figure 4:
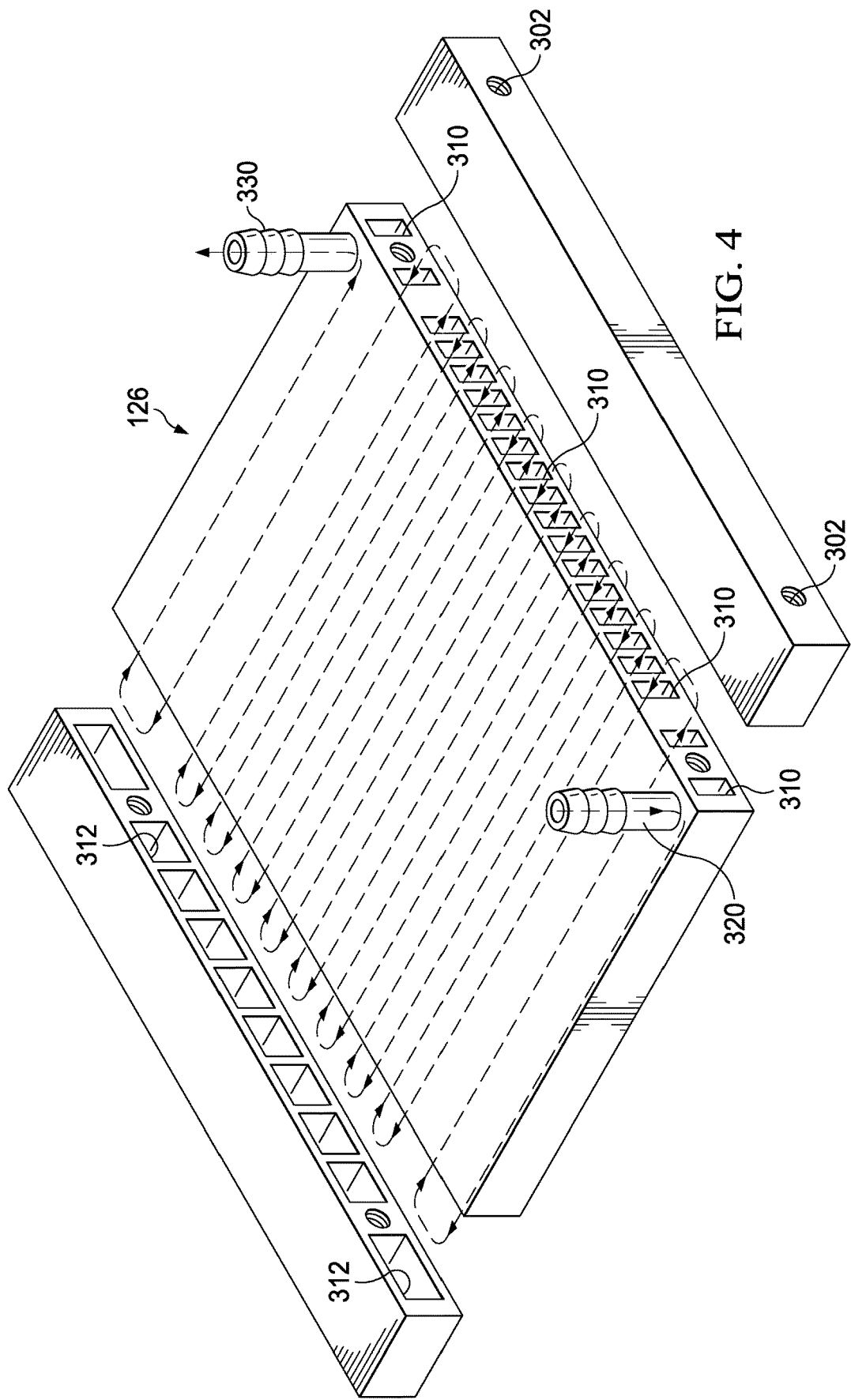
FIG. 4 illustrates an exploded view of a heat sink according to an embodiment of the disclosure.

FIGS. 3 and 4 illustrate detailed views of an exemplary heat sink 126 for use in a gas detector 100. The heat sink 126 may be a passive heat exchanger that transfers the heat generated by an electronic or a mechanical device (e.g., the electronic elements within the gas detector) to a fluid medium, often air or a liquid coolant (e.g., the sample gas), where it is dissipated away from the device, thereby allowing regulation of temperature of the device (e.g., gas detector) at optimal levels. In an example, the heat sink 126 is a passive component, where a passive heat sink 126 may not require an external energy source to dissipate the heat energy introduced to the heat sink by the surrounding electronic elements. The passive heat sink 126 may be made from a relatively cheap material with a high thermal conductivity, such as copper and/or aluminum, though other suitable materials may be used. A further advantage is, as the heat sink is passive, it does not require the extra cost and difficulty associated with incorporating and maintaining a power source.

As shown in FIGS. 3 and 4, the heat sink 126 may comprise an inlet 320 (configured to attach to the sample gas flow line 125), and an outlet 330 (configured to attach to the sample gas flow line 125). The heat sink 126 may comprise a plurality of elongated channels 310 extending between a plurality of ducts 312 configured to direct the sample gas flow through the heat sink 126 in the direction indicated by the arrows in FIG. 4. The ducts 312 may be configured to connect the channels 310, allowing the sample gas flow to continue through each of the channels 310 from the inlet 320 to the outlet 330.

In some embodiments, the heat sink 126 may comprise screw holes 302 configured to allow the heat sink 126 to be attached within the gas detector via one or more screws, where the channels 310 may be positioned around the screw holes 302. In some embodiments, the number of channels 310, the size of the channels 310, and the overall size of the heat sink 126 may be chosen based on the size of the gas detector, the expected heat that will need to be dissipated by the heat sink 126, and the available space within the housing of the gas detector.

Embodiments may include a method for dissipating heat from a gas detector. A sample gas flow may be provided to the gas detector. The sample gas flow may be directed through the gas detector and generated via a pump within the gas detector. The sample gas flow may be tested by a sensor within the gas detector, wherein the sensor may detect one or more potentially hazardous gases within the sample gas flow. In some embodiments, the sensor may communicate sensed data to a user via a user interface of the gas detector. After passing through the sensor, the sample gas flow may then be directed to the inlet of a heat sink located within the housing of the gas detector. The heat sink may be configured to transfer heat from the interior of the gas detector to the sample gas flow as it passes through the heat sink toward an outlet of the heat sink. Then, the sample gas flow may be directed out of the gas detector via an outlet of the gas detector. A method may also comprise adjusting the flow rate of the sample gas flow based on the desired heat transfer via the heat sink.

Having described various devices and methods herein, exemplary embodiments or aspects can include, but are not limited to:

In a first embodiment, a gas detector may comprise a housing configured to contain the elements of the gas detector; an airflow generator located within the housing and configured to generate a sample gas flow through the gas detector; a sample gas flow line configured to direct the sample gas flow within the housing of the gas detector from an inlet of the gas detector toward an outlet of the gas detector; a sensor, located within the housing and in fluid communication with the airflow generator via the sample gas flow line, configured to detect one or more potentially hazardous gases within the sample gas flow; and a heat sink, located within the housing in fluid communication with the airflow generator and positioned after the sensor along the sample gas flow line, configured to transfer heat from an interior of the housing to the sample gas flow, wherein the sample gas flow is directed out of the housing via the outlet of the gas detector.

A second embodiment can include the gas detector of the first embodiment, further comprising one or more electronic elements located within the housing, wherein the one or more electronic elements generate heat when operated.

A third embodiment can include the gas detector of the second embodiment, wherein the heat sink is located adjacent to one or more of the electronic elements.

A fourth embodiment can include the gas detector of any of the first through third embodiments, wherein the airflow generator comprises a pump.

A fifth embodiment can include the gas detector of any of the first through fourth embodiments, further comprising insulation of the heat sink, preventing the sample gas flow from escaping the heat sink into the interior of the housing.

A sixth embodiment can include the gas detector of any of the first through fifth embodiments, further comprising a user interface configured to display sensed data from the sensor.

A seventh embodiment can include the gas detector of any of the first through sixth embodiments, wherein the heat sink is located within a top portion of the housing.

An eighth embodiment can include the gas detector of any of the first through seventh embodiments, wherein the heat sink is positioned between the sensor and the outlet, along the sample gas flow line.

A ninth embodiment can include the gas detector of any of the first through eighth embodiments, wherein the heat sink comprises an inlet, an outlet, a plurality of channels located between the inlet and the outlet, and a plurality of ducts connecting the plurality of channels.

A tenth embodiment can include the gas detector of any of the first through ninth embodiments, wherein the heat sink is a passive heat sink.

In an eleventh embodiment, a method for dissipating heat from the interior of a gas detector may comprise generating a sample gas flow through the gas detector via an airflow generator from an inlet of the gas detector toward an outlet of the gas detector; testing, by a sensor within the gas detector, the sample gas flow for one or more potentially hazardous gases; after testing the sample gas flow by the sensor, directing the sample gas flow toward an inlet of a heat sink located within a housing of the gas detector; transferring heat from the interior of the housing to the sample gas flow via the heat sink; and directing the sample gas flow out of the gas detector via an outlet of the gas detector.

A twelfth embodiment can include the method of the eleventh embodiment, further comprising communicating the sensed data from the sensor to a user interface; and displaying, by the user interface, the sensed data to a user.

A thirteenth embodiment can include the method of the eleventh or twelfth embodiment, detecting, by the sensor, one or more potentially hazardous gases within the sample gas flow.

A fourteenth embodiment can include the method of any of the eleventh through thirteenth embodiments, further comprising adjusting the flow rate of the sample gas flow based on the desired heat transfer via the heat sink.

A fifteenth embodiment can include the method of any of the eleventh through fourteenth embodiments, further comprising preventing the sample gas flow from escaping from the heat sink into the interior of the housing of the gas detector.

In a sixteenth embodiment, a gas detector may comprise an inlet configured to receive a sample gas flow; an outlet configured to exhaust the sample gas flow from the gas detector; an airflow generator configured to generate the sample gas flow through the gas detector from the inlet toward the outlet; a sensor in fluid communication with the airflow generator, configured to detect one or more potentially hazardous gases within the sample gas flow; and a heat sink in fluid communication with the airflow generator, positioned between the sensor and the outlet in the direction of the sample gas flow, and configured to transfer heat from an interior of the gas detector to the sample gas flow.

A seventeenth embodiment can include the gas detector of the sixteenth embodiment, further comprising a sample gas flow line in fluid communication with the inlet, the outlet, the airflow generator, the sensor, and the heat sink, and configured to direct the sample gas flow within the housing of the gas detector.

An eighteenth embodiment can include the gas detector of the sixteenth or seventeenth embodiment, further comprising a housing configured to contain the elements of the gas detector, wherein the inlet receives the sample gas flow into the housing, and wherein the outlet directs the sample gas flow out of the housing.

A nineteenth embodiment can include the gas detector of any of the sixteenth through eighteenth embodiments, wherein the heat sink comprises an inlet, an outlet, a plurality of channels located between the inlet and the outlet, and a plurality of ducts connecting the plurality of channels.

A twentieth embodiment can include the gas detector of any of the sixteenth through nineteenth embodiments, wherein the sample gas flow contains one or more potentially hazardous gases.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises," "includes," and "having" should be understood to provide support for narrower terms such as "consisting of," "consisting essentially of," and "comprised substantially of" Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:
1. A gas detector comprising:
a housing configured to contain elements of the gas detector;
an airflow generator located within the housing and configured to generate a sample gas flow through the gas detector;
a sample gas flow line configured to direct the sample gas flow within the housing of the gas detector from an inlet of the gas detector toward an outlet of the gas detector;
a sensor, located within the housing and in fluid communication with the airflow generator via the sample gas flow line, configured to detect one or more potentially hazardous gases within the sample gas flow; and
a heat sink, located within the housing in fluid communication with the airflow generator and positioned after the sensor along the sample gas flow line, configured to transfer heat from an interior of the housing to the sample gas flow, wherein the sample gas flow is directed out of the housing via the outlet of the gas detector.

2. The gas detector of claim 1, further comprising one or more electronic elements located within the housing, wherein the one or more electronic elements generate heat when operated.

3. The gas detector of claim 2, wherein the heat sink is located adjacent to one or more of the electronic elements.

4. The gas detector of claim 1, wherein the airflow generator comprises a pump.

5. The gas detector of claim 1, further comprising insulation of the heat sink, preventing the sample gas flow from escaping the heat sink into the interior of the housing.

6. The gas detector of claim 1, further comprising a user interface configured to display sensed data from the sensor.

7. The gas detector of claim 1, wherein the heat sink is located within a top portion of the housing.

8. The gas detector of claim 1, wherein the heat sink is positioned between the sensor and the outlet, along the sample gas flow line.

9. The gas detector of claim 1, wherein the heat sink comprises an inlet, an outlet, a plurality of channels located between the inlet and the outlet, and a plurality of ducts connecting the plurality of channels.

10. The gas detector of claim 1, wherein the heat sink is a passive heatsink.

11. A method for dissipating heat from an interior of a gas detector, the method comprising:
 generating a sample gas flow through the gas detector via an airflow generator from an inlet of the gas detector toward an outlet of the gas detector;
 testing, by a sensor within the gas detector, the sample gas flow for one or more potentially hazardous gases;
 after testing the sample gas flow by the sensor, directing the sample gas flow toward an inlet of a heat sink located within a housing of the gas detector;
 transferring heat from an interior of the housing to the sample gas flow via the heat sink; and
 directing the sample gas flow out of the gas detector via the outlet of the gas detector.

12. The method of claim 11, further comprising communicating sensed data from the sensor to a user interface; and displaying, by the user interface, the sensed data to a user.

13. The method of claim 11, further comprising detecting, by the sensor, one or more potentially hazardous gases within the sample gas flow.

14. The method of claim 11, further comprising adjusting a flow rate of the sample gas flow based on a desired heat transfer via the heat sink.

15. The method of claim 11, further comprising preventing the sample gas flow from escaping from the heat sink into the interior of the housing of the gas detector.

16. A gas detector comprising:
 an inlet configured to receive a sample gas flow;
 an outlet configured to exhaust the sample gas flow from the gas detector;
 an airflow generator configured to generate the sample gas flow through the gas detector from the inlet toward the outlet;
 a sensor in fluid communication with the airflow generator, configured to detect one or more potentially hazardous gases within the sample gas flow; and
 a heat sink in fluid communication with the airflow generator, positioned between the sensor and the outlet in a direction of the sample gas flow, and configured to transfer heat from an interior of the gas detector to the sample gas flow.

17. The gas detector of claim 16, further comprising a sample gas flow line in fluid communication with the inlet, the outlet, the airflow generator, the sensor, and the heat sink, and configured to direct the sample gas flow within a housing of the gas detector.

18. The gas detector of claim 16, further comprising a housing configured to contain elements of the gas detector, wherein the inlet receives the sample gas flow into the housing, and wherein the outlet directs the sample gas flow out of the housing.

19. The gas detector of claim 16, wherein the heat sink comprises an inlet, an outlet, a plurality of channels located between the inlet and the outlet, and a plurality of ducts connecting the plurality of channels.

20. The gas detector of claim 16, wherein the sample gas flow contains one or more potentially hazardous gases.

* * * * *